US00PP24830P3

(12) United States Plant Patent
Olesen

(10) Patent No.: US PP24,830 P3
(45) Date of Patent: Sep. 2, 2014

(54) COMPACT FLORIBUNDA ROSE PLANT NAMED 'POULCAS038'

(50) Latin Name: ***Rosa* hybrid**
Varietal Denomination: Poulcas038

(75) Inventor: Mogens Nyegaard Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 42 days.

(21) Appl. No.: 13/507,024

(22) Filed: May 31, 2012

(65) Prior Publication Data

US 2013/0326764 P1 Dec. 5, 2013

(51) Int. Cl.
*A01H 5/00* (2006.01)

(52) U.S. Cl.
USPC ..... Plt./148; Plt./101; Plt./141

(58) Field of Classification Search
USPC ..... Plt./101, 141, 148
See application file for complete search history.

*Primary Examiner* — Susan McCormick Ewoldt

(57) ABSTRACT

A new garden rose plant of the Compact Floribunda class which has abundant, pink flowers and attractive foliage. This new and distinct variety has shown to be uniform and stable in the resulting generations from asexual propagation.

2 Drawing Sheets

Botanical designation: *Rosa* hybrid.
Variety denomination: 'Poulcas038'.

SUMMARY OF THE INVENTION

The present invention constitutes a new and distinct variety of garden rose plant which originated from a controlled crossing between the female seed parent, an unnamed seedling, and the male pollen parent, also an unnamed seedling.

The two parents were crossed during the summer of 2003 and the resulting seeds were planted in a controlled environment in Fredensborg, Denmark. The new variety, named 'Poulcas038', originated as a single seedling from the stated cross.

The new variety may be distinguished from its male pollen parent and female seed parent primarily by flower coloration and growth habit.

The objective of the hybridization of this rose variety was to create a new and distinct variety for garden use with unique qualities, such as:

1. Uniform and abundant pink flowers;
2. Vigorous, but compact growth when propagated both as a budded rose and on its own roots;
3. Exceptional disease resistance.

This combination of qualities is not present in previously available commercial cultivars of this type, known to the inventor, and distinguish 'Poulcas038' from all other varieties of which we are aware.

As part of the rose development program, Mogens N. Olesen germinated the seeds from the aforementioned hybridization during winter of 2003 and conducted evaluations on the resulting seedlings in a controlled environment in Fredensborg, Denmark. 'Poulcas038' was selected in the spring of 2004 by the inventor as a single plant from the progeny of the aforementioned hybridization.

Asexual reproduction of 'Poulcas038' by traditional budding and rooted cuttings was first done by Mogens N. Olesen in the nursery in Fredensborg, Denmark in July, 2004. This initial and other subsequent asexual propagations conducted in controlled environments have demonstrated that the characteristics of 'Poulcas038' are true to type and are transmitted from one generation to the next.

DESCRIPTION OF THE DRAWING

The accompanying color illustrations show as true as is reasonably possible to obtain in color photographs of this type, the typical characteristics of the buds, flowers, leaves, and stems, of 'Poulcas038'.

Specifically illustrated in FIG. 1 are flowers at various stages of development, flower in parts, leaves, and stems.

DETAILED DESCRIPTION OF THE VARIETY

Figure 1:
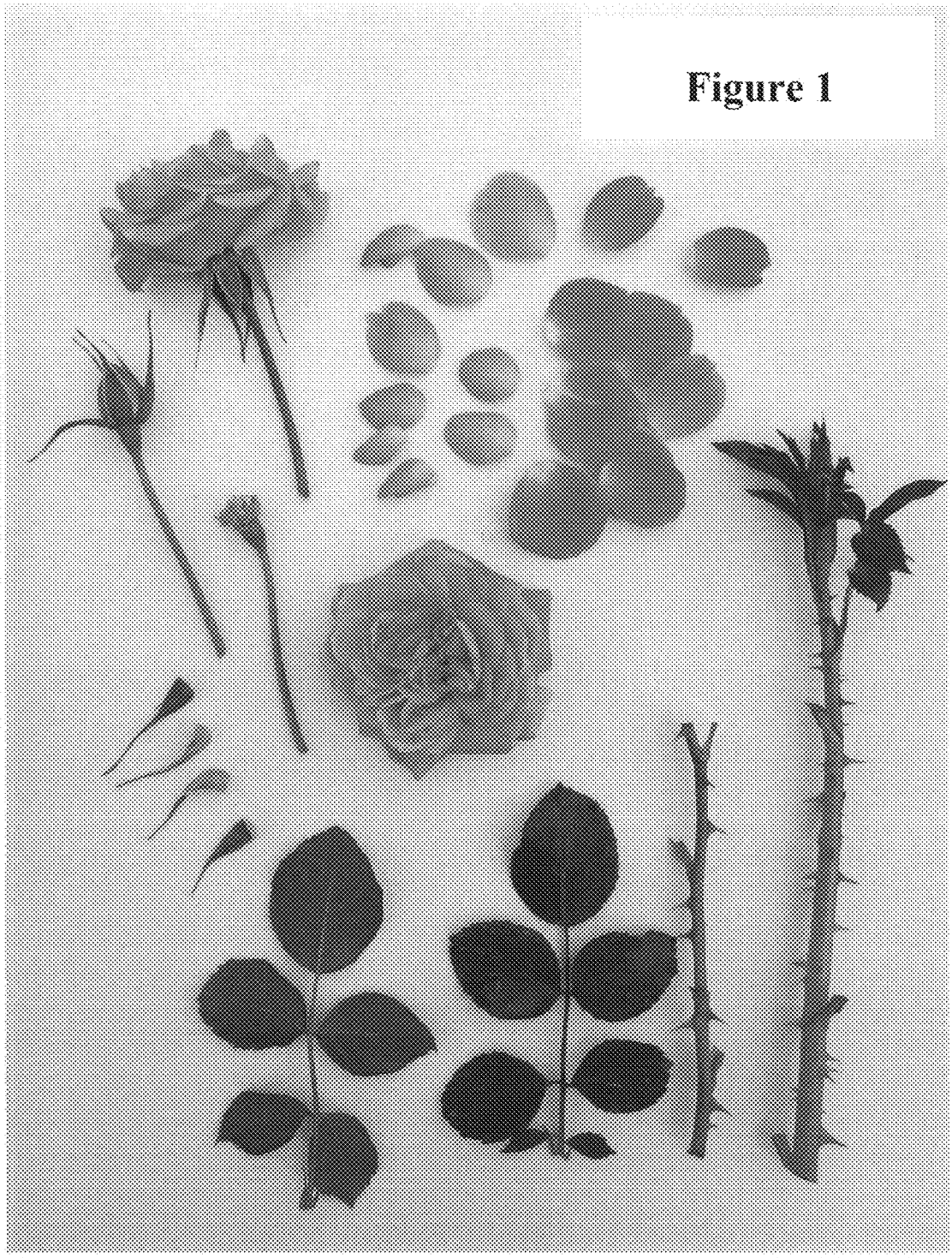
Figure 2:
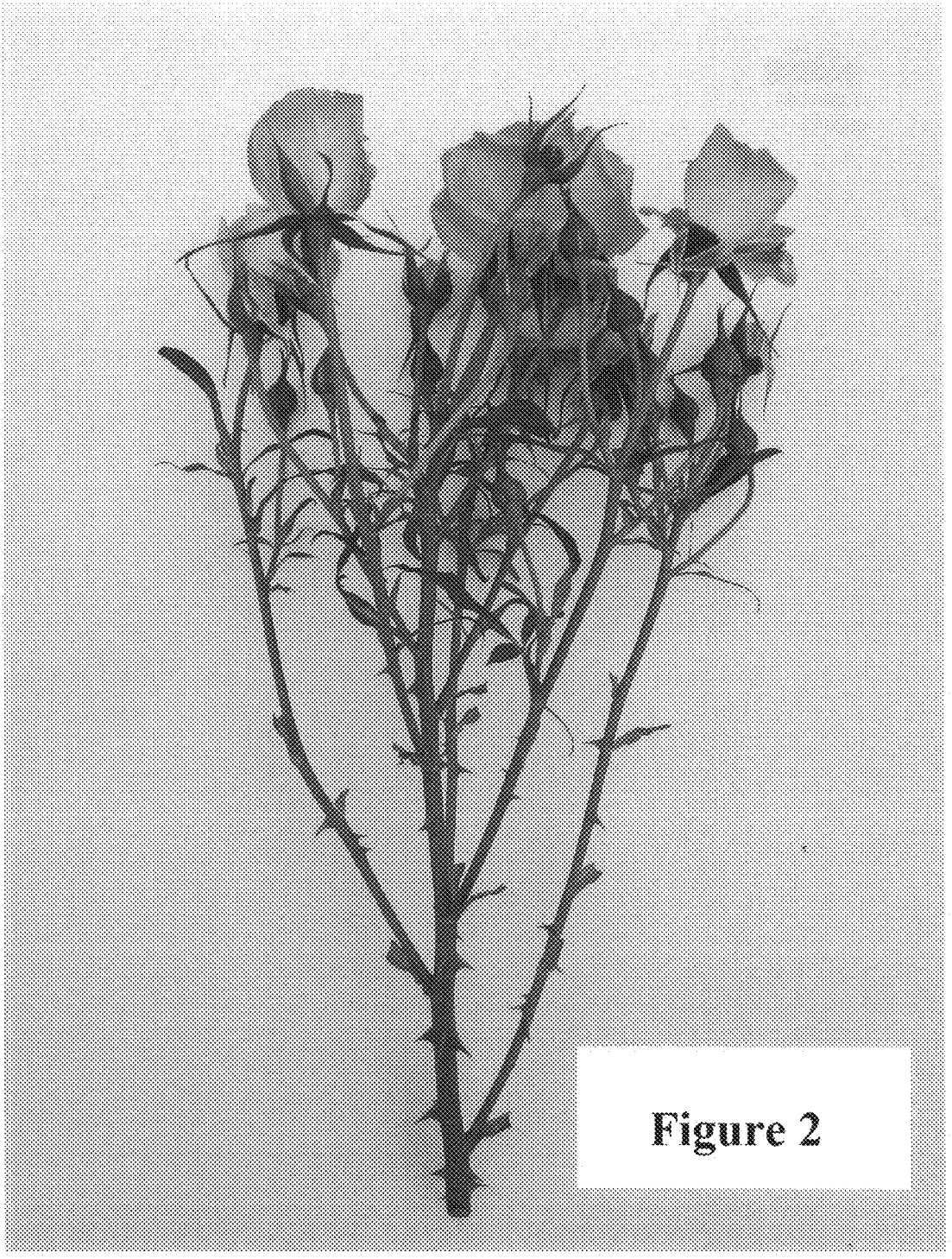
FIG. 2 illustrates the arrangement of peduncles and flowers on a flowering branch. The illustrated plant is 2 years of age.

The following is a description of 'Poulcas038', as observed in its growth in in a field nursery in Marion County, Oreg. Observed plants are 3 years of age, and were grown on their own roots. Color references are made using The Royal Horticultural Society (London, England) Colour Chart, 2001, except where common terms of color are used.

For a comparison, several physical characteristics of the rose variety 'Poulriber', U.S. Plant Pat. No. 12,902 are compared to 'Poulcas038' in Chart 1.

CHART 1

| | 'Poulcas038' | 'Poulriber' |
|---|---|---|
| Petal Count | 60, 10 of which are petaloids | 18-22 petals under normal conditions with 4-6 petaloids |
| Flower Diameter | 65 mm | 65-75 mm |
| Genaral Tonality of Flower Color | Open flowers are Red Group 55A to 52C. | Red Group 40C-41B |

FLOWER AND FLOWER BUD

Blooming habit: Continuous.

Flower bud:

*Size*.—Upon opening, 25 mm in length from base of receptacle to end of bud. Bud diameter is 14 mm.

*Bud form*.—Urceolate.

*Bud color*.—As sepals divide petals are Red-Purple Group 58B.

*Sepal inner surface*.—Color: Green Group 138C to 138B. Surface: Smooth and strongly pubescent.

*Sepal outer surface*.—Color: Yellow-Green Group 144A. Texture: Smooth.

*Sepal shape*.—Apex: Cirrhose. Base: Flat at union with receptacle.

*Sepal margin*.—Margins have weak foliaceous appendages on three of the five sepals.

*Sepal size*.—35 mm long by 6 mm wide.

*Receptacle*.—Texture: Smooth. Shape: Urn shaped. Size: 7 mm tall by 5 mm wide. Color: Yellow-Green Group 144A.

*Pedicel*.—Surface: Smooth. Length: 40 to 65 mm. Diameter: 3 mm on average. Color: Yellow-Green Group 145A. Strength: Strong.

*Peduncle*.—Length: 2 to 18 cm. Diameter: 4 mm. Color: Yellow-Green Group 145A.

Flower bud development: Flower buds are borne in clusters of 5 to 7 flower buds per stem, resembling a panicle.

Flower bloom:

*Fragrance*.—None.

*Duration*.—The blooms have a duration on the plant of approximately 10 days. Petals fall cleanly away from plant after flowers have fully matured.

*Size*.—Flower diameter is 65 mm when open. Flower depth is 28 mm.

*Flower shape*.—General shape is a rosette, very double flower with many slightly overlapping petals of different sizes.

*Shape of flower, side view*.—Upon opening the upper portion is flat. The lower portion is concave.

Petalage: Under normal conditions, flowers have 60 petals total, 10 of which are petaloids.

Petal color:

*Upon opening, outer petals*.—Upper surface: Red Group 52B. Lower surface: Red Group 52C splashed with intonations of Red Group 49B.

*Upon opening, inner petals*.—Upper surface: Red Group 50A. Lower surface: Red Group 50B.

*Basal petal spots, upon opening*.—Upper surface: Yellow Group 4B. Lower surface: Yellow Group 4B.

*After opening, outer petals*.—Upper surface: Red Group 52B. Lower surface: Red Group 55B.

*After opening, inner petals*.—Upper surface: Red Group 52C. Lower surface: Red Group 55B.

*Basal petal spots, after opening*.—Upper surface: Yellow Group 4C. Lower surface: Yellow Group 4C.

General tonality: Open flowers are Red Group 55A to 52C. Tonality remains the same through the duration of the flower.

Petals:

*Petal reflex*.—Moderate.

*Margin*.—Entire and uniform with a point at the center. Moderate undulations of margin observed.

*Shape*.—Generally narrow elliptic. Apex shape: Rounded. Base shape: Acute.

*Size*.—32 mm (l) 32 mm (w).

*Texture*.—Smooth.

*Thickness*.—Average.

Petaloids:

*Quantity*.—10 on average.

*Shape*.—Elliptic, with a rounded apex and acute base shape.

*Color*.—Upper surface is Red Group 43C. The lower surface is Red Group 43D. Petal base spots are Yellow Group 5C.

*Size*.—14 mm (l)×16 mm (w).

Reproductive organs:

*Pollen*.—None observed.

*Anthers*.—Size: 2 mm in length. Color: Red Group 39C. Quantity: 35 on average.

*Filaments*.—Color: Yellow Group 10B. Length: 5 mm.

*Pistils*.—Length: 7 mm. Quantity: 25 on average.

*Stigmas*.—Color: Yellow-White Group 158A.

*Styles*.—Color: Orange Group 27D.

*Location of stigmas*.—Superior in location relative to the length of the filaments and the height of the anthers.

*Hips*.—None Observed.

PLANT

Plant growth: Upright, bushy. Plants are 45 cm in height, and 45 cm wide on average.

Stems:

*Color*.—Juvenile growth: Yellow-Green Group 145B. Mature growth: Yellow-Green Group 146C.

*Length*.—On average, canes are 35 cm from the base of the plant to the flowering portion.

*Diameter*.—9 mm.

*Internodes*.—On mature canes, there is an average distance of 40 mm between nodes.

*Surface texture*.—Young wood: Smooth. Older wood: Smooth.

Long prickles:

*Incidence*.—10 prickles per 10 cm of stem.

*Size*.—Average length of prickles on mature stems is 10 mm.

*Shape*.—Upper portion is linear. Lower portion is concave.

*Color*.—Juvenile prickles: Yellow-Green Group 144B with intonations of Greyed-Red Group 181A. Mature prickles: Yellow-Green Group 144A.

Plant foliage:

*Compound leaf*.—125 mm (l)×75 (w).

*Quantity*.—2 leaves per 10 cm of stem on average.

*Color of juvenile foliage*.—Upper side: Greyed-Purple Group 183A. Lower side: Greyed-Purple Group 187A.

*Color of mature foliage*.—Upper side: Yellow-Green Group 147A. Lower side: Yellow-Green Group 147B.

Plant leaves and leaflets:

*Stipules*.—Size: 20 mm in length. 5 mm wide. Quantity: 2 per compound leaf. Shape: Linear, slightly broad based with outward extending apices. Margins: Finely serrated. Color: Yellow-Green Group 146A.

*Petiole*.—Length: 20 mm. Diameter: 2 mm.

*Upper surface*.—Color: Green Group 138A.

*Lower surface*.—Color: Yellow-Green Group 144B. Observations: Few stipitate glands and prickles observed.

*Rachis*.—Length: 60 mm. Upper surface: Color: Green Group 138A.

*Lower surface*.—Color: Yellow-Green Group 144B. Observations: Few stipitate glands and prickles observed.

*Leaflet*.—Quantity: Normal number of leaflets per leaf in middle of the stem is 5 leaflets. Margins: Serrated. Size: Average size of the terminal leaflet on normal leaves is 45 mm in length by 30 mm wide. Shape: Generally elliptical. Base: Rounded. Apex: Mucronate. Texture: Smooth. Thickness: Average. Arrangement: Odd pinnate. Venation: Reticulate. Glossiness: Very glossy.

Disease resistance: Above average resistance to powdery and downy mildew, rust, black spot, and *Botrytis* under normal growing conditions.

Cold hardiness: The variety is tolerant to USDA Cold Hardiness Zone 6.

Heat tolerance: The variety has been found to be suitable for climate conditions found in the American Horticulture Society heat zone 7.

The invention claimed is:

1. A new and distinct variety of rose plant of the Compact Floribunda rose class named 'Poulcas038', substantially as illustrated and described herein, due to its abundant pink flowers, disease resistance, and extended period of bloom.

* * * * *